US006682507B2

(12) United States Patent
Irish

(10) Patent No.: US 6,682,507 B2
(45) Date of Patent: Jan. 27, 2004

(54) USER WEARABLE DEVICE HAVING STERILE ENVIRONMENT FOR CONNECTING PERITONEAL DIALYSIS TUBES

(75) Inventor: Douglas H. Irish, Mt. Morris, MI (US)

(73) Assignee: Doug's Kangaroo Pouch, LLC, Flint, MI (US)

( * ) Notice: Subject to any disclaimer, the term of this patent is extended or adjusted under 35 U.S.C. 154(b) by 0 days.

(21) Appl. No.: 10/079,368

(22) Filed: Feb. 20, 2002

(65) Prior Publication Data
US 2003/0158528 A1 Aug. 21, 2003

(51) Int. Cl.[7] .............................................. A61M 5/32
(52) U.S. Cl. ...................................... 604/179
(58) Field of Search ....................... 604/179, 174, 604/345, 29, 533, 180, 183; 128/DIG. 6; 383/210

(56) References Cited

U.S. PATENT DOCUMENTS

| | | | |
|---|---|---|---|
| 3,472,369 A | * 10/1969 | Schuster | 383/210 |
| 4,582,508 A | 4/1986 | Pavelka | |
| 4,767,405 A | 8/1988 | Lokken | |
| 4,799,923 A | * 1/1989 | Campbell | 604/179 |
| 4,955,867 A | 9/1990 | Endo | |
| 5,425,719 A | * 6/1995 | Lessing, Jr. | 604/179 |
| 5,468,229 A | 11/1995 | Chandler | |
| 5,496,282 A | 3/1996 | Militzer et al. | |
| 5,671,983 A | * 9/1997 | Miller et al. | 312/1 |
| 5,688,248 A | 11/1997 | Lessing, Jr. | |
| 5,758,660 A | 6/1998 | Lokken | |
| 5,843,132 A | 12/1998 | Ilvento | |
| 5,853,396 A | * 12/1998 | Bennes et al. | 604/179 |
| 6,027,489 A | 2/2000 | Galato | |
| 6,126,639 A | 10/2000 | Sutherland et al. | |

FOREIGN PATENT DOCUMENTS

FR           0807449 A1 * 11/1996 .......... A61M/25/02

* cited by examiner

Primary Examiner—Michael J. Hayes
Assistant Examiner—Lina R Kontos
(74) Attorney, Agent, or Firm—Brooks Kushman P.C.

(57) ABSTRACT

A user wearable device for providing a sterile environment for connecting a user's catheter to a fill-drain tube for performing an exchange of used and fresh peritoneal dialysis fluid includes a pouch. The pouch has exposeable openings for inserting the catheter and a fill-drain tube into the interior of the pouch from the exterior of the pouch. The user connects the catheter to the fill-drain tube within the interior of the pouch for draining and feeding dialysis fluid in a sterile environment. Hand covering elements in communication with the exterior of the pouch are disposed internal to the pouch such that the user can insert his hands into the hand covering elements and connect the catheter to the fill-drain tube within the interior of the pouch. The hand covering elements enable the user to manipulate the catheter and the fill-drain tube from a non-sterile environment external to the pouch.

27 Claims, 4 Drawing Sheets

USER WEARABLE DEVICE HAVING STERILE ENVIRONMENT FOR CONNECTING PERITONEAL DIALYSIS TUBES

BACKGROUND OF THE INVENTION

1. Field of the Invention

The present invention relates generally to continuous ambulatory peritoneal dialysis (CAPD) methods and systems and, more particularly, to a user wearable device such as a pouch or bag which provides a sterile environment for connecting a catheter to a fill-drain tube for feeding and draining dialysis fluid.

2. Background Art

Continuous ambulatory peritoneal dialysis (CAPD) is a method for performing dialysis for users with kidney failure. CAPD occurs in the user's peritoneal cavity using dialysis fluid. CAPD functions the same way kidneys do by constantly cleansing the blood as long as there is dialysis fluid in the peritoneal cavity. The dialysis fluid is left in the peritoneal cavity for several hours to collect waste from the blood. The used dialysis fluid is then drained from the peritoneal cavity into a drain bag. Fresh dialysis fluid from a fill bag is then supplied into the peritoneal cavity for the process to start over.

In order to exchange used and fresh dialysis fluid in the peritoneal cavity, a catheter tube (catheter) is permanently attached to the user. An interior end of the catheter is surgically inserted through the user's abdomen into the user's peritoneal cavity. An exterior end of the catheter extends out about four inches from the user's abdomen. The user connects the exterior end of the catheter to the fill bag via a fill-drain tube for receiving fresh dialysis fluid into the user's peritoneal cavity. Similarly, the user connects the exterior end of the catheter tube to the drain bag via the fill-drain tube for draining used dialysis fluid from the user's peritoneal cavity. Once the draining and filling operations are completed, the user disconnects the catheter from the fill-drain tube and seals the catheter.

The user must repeatedly exchange used and fresh dialysis fluid about four times a day for CAPD. Each exchange encompasses connecting the exterior end of the catheter tube to the fill-drain tube. A problem with each exchange is that the user must make the connections such that no germs or bacteria are introduced into the catheter tube. Germs or bacteria introduced into the catheter can enter the peritoneal cavity and cause infection. Repeated infections scar the peritoneal cavity and cause pain to the user.

In order to ensure that no germs or bacteria are introduced into the catheter, the user must perform what is known as the "aseptic technique" for making the connection between the catheter and the fill-drain tube. The aseptic connection technique includes making the connection between the catheter and the fill-drain tube in a closed environment such as a room. All doors, windows, and vents in the room must be closed and all fans in the room turned off in order to keep the air movement in the room at a minimum. The room should also be void of family activity and pets and occur in a spare bedroom or the like. In general, the aseptic connection technique requires appropriate environmental conditions which limit the mobility and flexibility of the user and require limitations on space resources.

What is needed is a portable device which effectively consolidates the size of a typical closed environment such as a spare bedroom into a much smaller size. Such a portable device would provide a sterile environment for connecting the catheter to the fill-drain tube for an exchange of used and fresh dialysis fluid even when the user is located in an environment unsuitable for the aseptic connection technique. As a result, a user wearing such a portable device while situated within a hostile environment, such as room where the windows are open or on a boat in a lake, could connect the dialysis tubes in order to perform an exchange in a sterile environment thereby satisfying the aseptic connection technique.

SUMMARY OF THE INVENTION

Accordingly, it is an object of the present invention to provide a user wearable portable device such as a pouch or bag which provides a sterile environment for connecting the user's catheter to a fill-drain tube for performing an exchange of used and fresh dialysis fluid.

It is another object of the present invention to provide a user wearable pouch which provides a sterile environment for connecting the user's catheter to a fill-drain tube for performing an exchange of used and fresh dialysis fluid.

It is a further object of the present invention to provide a user wearable pouch having openings for inserting the user's catheter and a fill-drain tube into the interior of the pouch such that the user can connect the catheter to the fill-drain tube within the interior of the pouch for draining and feeding dialysis fluid in a sterile environment.

It is still another object of the present invention to provide a user wearable pouch having covered openings for inserting the user's catheter and a fill-drain tube into the interior of the pouch and having internally disposed hand covering elements in communication with the exterior of the pouch such that the user can insert his hands into the hand covering elements and connect the catheter to the fill-drain tube within the interior of the pouch for performing an exchange of used and fresh dialysis fluid in a sterile environment.

It is still a further object of the present invention to provide a user wearable pouch having covered openings for inserting a user's catheter and a fill-drain tube into respective sleeves extending into the interior of the pouch such that the user can expose the catheter and the fill-drain tube from the respective sleeves within the interior of the pouch and connect the catheter to the fill-drain tube within the interior of the pouch for performing an exchange of used and fresh dialysis fluid in a sterile environment.

It is still yet another object of the present invention to provide a user wearable pouch having a sterile interior operable for receiving a catheter and a fill-drain tube from sources exterior to the pouch such that the user can connect the catheter and the fill-drain tube in a sterile environment.

It is still yet a further object of the present invention to provide a user wearable pouch having internally disposed hand covering elements for enabling the user to insert his hands into the hand covering elements and connect the user's catheter to a fill-drain tube in the sterile interior of the pouch while manipulating the catheter and the fill-drain tube from a non-sterile environment external to the pouch.

Yet, it is still another object of the present invention to provide a peritoneal dialysis system having a user wearable pouch which provides a sterile environment for connecting the user's catheter to a fill-drain tube connected to a fill bag and a drain bag for performing an exchange of used and fresh dialysis fluid.

Yet, it is a further object of the present invention for providing a method for performing an exchange of used and fresh dialysis fluid by connecting a user's catheter to a fill-drain tube within the interior of a user wearable portable device.

In carrying out the above objects and other objects, the present invention provides a user wearable device for connecting a catheter of the user to a fill-drain tube for performing an exchange of dialysis fluid. The device includes a pouch having an interior formed by connected front and back sides. The front side of the pouch has an exposeable opening for inserting a fill-drain tube into the interior of the pouch. The back side of the pouch has an exposeable opening for inserting a catheter into the interior of the pouch.

The device may include at least one internally disposed hand covering element in communication with the exterior of the pouch for receiving at least one of the user's hands in order to enable the user to connect the catheter to the fill-drain tube within the interior of the pouch for performing an exchange of dialysis fluid. The at least one internally disposed hand covering element may include a pair of mittens.

A fill-drain tube sleeve extending into the interior of the pouch for receiving the fill-drain tube when the fill-drain tube is inserted into the interior of the pouch may be connected to the exposeable opening of the front side of the pouch. A catheter sleeve extending into the interior of the pouch for receiving the catheter when the catheter is inserted into the interior of the pouch may be connected to the exposeable opening of the back side of the pouch. The exposeable openings may each include a peel away seal.

Attachment means may be connected to the pouch for attaching the pouch to the user. The attachment means may include a pair of strings connected to at least one of the front and back sides of the pouch for attaching the pouch around the user. The attachment means may include an adhesive attached to the back side of the pouch. The adhesive may be positioned around the exposeable opening of the back side of the pouch.

At least one of the pouch, the at least one internally disposed hand covering element, the fill-drain tube sleeve, and the catheter sleeve may be plastic and may be of a different color than any of the other elements. A catheter clamp may be connected to one of the front and back sides of the pouch within the interior of the pouch.

Further, in carrying out the above objects and other objects, the present invention provides a user wearable device for connecting an external end of a catheter connected to a user to a first end of a fill-drain tube connected at a second end to a fill bag and a drain bag for performing an exchange of dialysis fluid. The device includes a pouch having a closed interior, a first exposeable opening for inserting a first end of a fill-drain tube from an exterior of the pouch into the interior of the pouch, and a second exposeable opening for inserting an external end of a catheter of a user from the exterior of the pouch into the interior of the pouch. The device further includes a pair of hand covering elements in communication with the exterior of the pouch and internally disposed into the interior of the pouch for receiving the hands of the user in order to enable the user to connect the external end of the catheter to the first end of the fill-drain tube within the interior of the pouch for performing an exchange of dialysis fluid.

Also, in carrying out the above objects and other objects, the present invention provides a peritoneal dialysis system for a user having a catheter. The system includes a fill bag for feeding dialysis fluid, a drain bag for draining dialysis fluid, and a fill-drain tube connected at a first end by a Y connection to the fill bag and the drain bag. The system further includes a user wearable device having a closed pouch. The pouch has a first exposeable opening for inserting a second end of the fill-drain tube into the pouch and a second exposeable opening for inserting a catheter of a user wearing the pouch into the pouch in order to enable the catheter and the second end of the fill-drain tube to be connected together within the pouch by manipulation from outside of the pouch.

Still further, in carrying out the above objects and other objects, the present invention provides a method for performing an exchange of used and fresh dialysis fluid on a user having a catheter. The method includes providing a closed pouch having a first exposeable opening and a second exposeable opening. A catheter of the user is then inserted into pouch through the first exposeable opening. A fill-drain tube is then inserted into the pouch through the second exposeable opening. The catheter and the fill-drain tube are then connected together in the pouch by manipulation of the catheter and the fill-drain tube from outside of the pouch.

The method may further include attaching the pouch to the user after the catheter is inserted into the pouch through the first exposeable opening. The pouch may be attached to the user by using an adhesive positioned around the first exposeable opening on the outside of the pouch and then attaching the adhesive to the user around the catheter.

The method may also include connecting the catheter to the fill-drain tube by using a pair of hand covering elements in communication with the exterior of the pouch and internally disposed into the interior of the pouch for receiving the hands of the user.

The pouch may further include a catheter clamp in the pouch. The method may further include clamping the catheter with the catheter clamp prior to connecting the catheter to the fill-drain tube and removing the catheter clamp from the catheter after connecting the catheter to the fill-drain tube.

The advantages accruing to the present invention are numerous. For instance, the present invention provides a disposable and portable accessory that reduces the risk of peritonitis due to environmental contaminants carried in the air; increases the flexibility of scheduling exchanges outside of the traditional aspectic environment such as a spare bedroom thereby increasing the user's mobility; provides a safe, pathogenic-free environment for dialysis fluid exchanges; and increases the desirability of peritoneal dialysis as a method of treating renal disease.

In essence, the present invention provides for the flexibility of doing a safe dialysis fluid exchange at any time in any environment setting. For example, users of the present invention do not need to worry about the surrounding environmental conditions for performing a safe dialysis fluid exchange (i.e., closed room with no other people in the room, ventilation system off, window closed, clean surface to lay supplies on, and antibacterial hand washing). This enables users to not want to skip treatment because of an event keeping the user away from a set location for performing a dialysis exchange or in the case where the surrounding environmental conditions are adverse. The present invention further reduces the need for setting aside a location such as a room dedicated to having the appropriate environmental conditions.

DETAILED DESCRIPTION OF THE PREFERRED EMBODIMENT(S)

Figure 1:
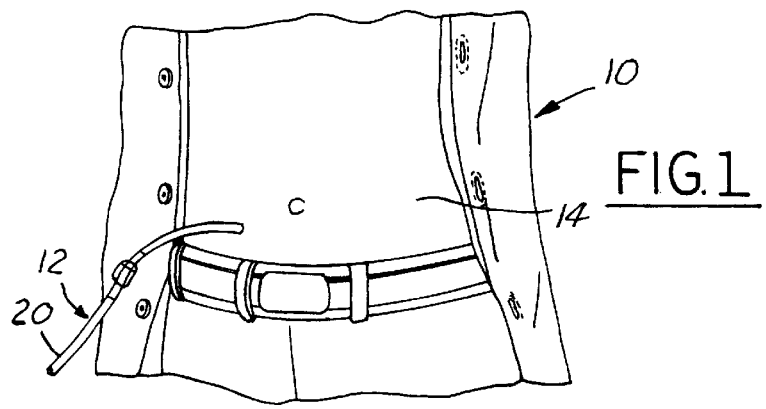
FIG. 1 illustrates a user having a catheter extending out from the user's abdomen.
Figure 2:
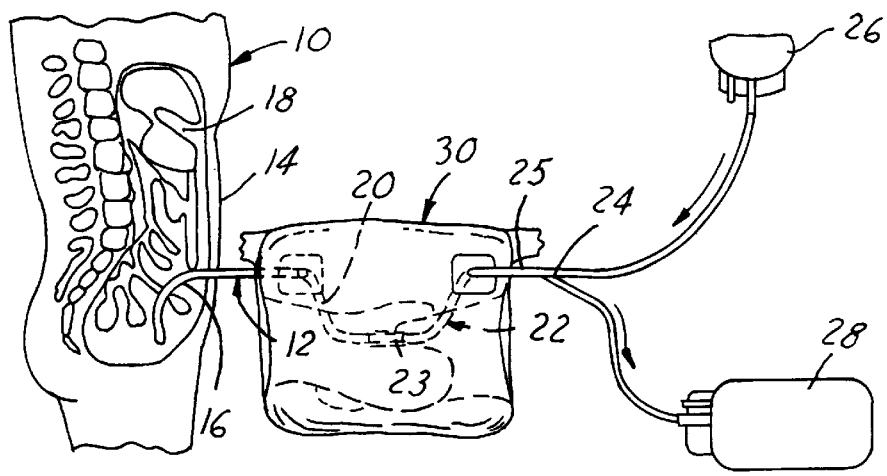
FIG. 2 illustrates the exchange of used dialysis fluid from the peritoneal cavity of the user and fresh dialysis fluid into the peritoneal cavity of the user via a user wearable device in accordance with the present invention.
Figure 5:
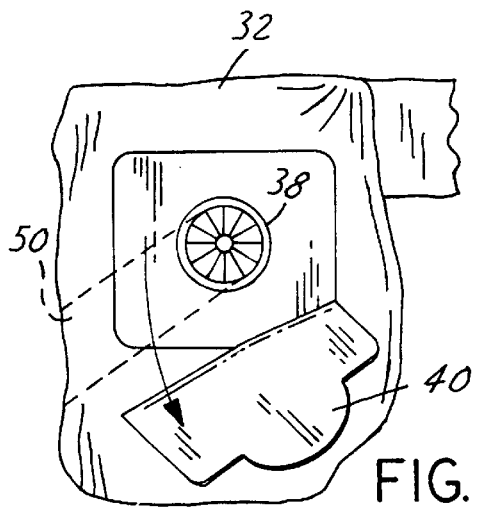
FIG. 5 illustrates the first exposeable opening on the front side of the user wearable device for receiving a fill-drain tube.
Figure 6:
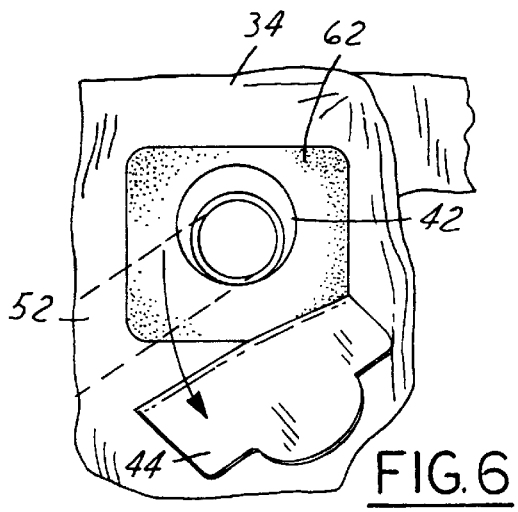
FIG. 6 illustrates the second exposeable opening on the back side of the user wearable device facing towards the user for receiving an external end of a user's catheter.

Referring now to FIGS. 1 and 2, a continuous ambulatory peritoneal dialysis (CAPD) user 10 having a catheter tube (catheter) 12 is shown. Catheter 12 is permanently attached to the abdomen 14 of user 10. An internal end 16 of catheter 12 is surgically inserted through abdomen 14 of user 10 into the user's peritoneal cavity 18. An external end 20 of catheter 12 extends externally out from abdomen 14 of user 10.

User 10 uses catheter 12 to exchange used dialysis fluid in peritoneal cavity 18 for fresh dialysis fluid. User 10 connects external end 20 of catheter 12 to a first end 23 of a fill-drain tube 22. A Y connector 24 connects a second end 25 of fill-drain tube 22 to a fill bag 26 and a drain bag 28. Fill bag 26 contains fresh dialysis fluid for insertion into peritoneal cavity 18 of user 10. Drain bag 28 is used to contain used dialysis fluid drained from peritoneal cavity 18 of user 10.

In order to perform CAPD, user 10 connects external end 20 of catheter 12 to drain bag 28 via fill-drain tube 22 for draining used dialysis fluid from user's peritoneal cavity 18. The used dialysis fluid drains from user's peritoneal cavity 18 into drain bag 28 in the direction of the arrow pointing to the drain bag shown in FIG. 2. Once the used dialysis fluid is drained from user's peritoneal cavity 18, user 10 connects external end 20 of catheter 12 to fill bag 26 via fill-drain tube 22 for receiving fresh dialysis fluid into the user's peritoneal cavity. The fresh dialysis fluid fills from fill bag 26 into user's peritoneal cavity 18 in the direction of the arrow pointing away from the fill bag shown in FIG. 2. Once the draining and filling operations are completed, user 10 disconnects external end 20 of catheter 12 from fill-drain tube 22 and seals the external end of the catheter. The fresh dialysis fluid is then left in user's peritoneal cavity 18 to clean the user's body and the process starts over once the fresh dialysis fluid becomes used.

As described above, user 10 is required to use the aseptic technique for making the connection between external end 20 of catheter 12 and first end 23 of fill-drain tube 22, i.e., connecting the catheter to the fill-drain tube. This means that catheter 12 and fill-drain tube 22 must be connected together in a sterile environment.

Referring now to FIGS. 3, 4, 5, 6, and 7, with continual reference to FIGS. 1 and 2, a user wearable device 30 which provides a sterile environment for connecting catheter 12 to fill-drain tube 22 is shown. In general, device 30 is a closed pouch or bag made of plastic or the like. Preferably, the plastic is the type of plastic typically used for medical and sterile applications. Of course, other types of material instead of plastic may be used for making pouch 30.

Pouch 30 includes a front side 32 and a back side 34 connected together around their edges to form an interior 36 within the internal sides of the front and back sides. Front side 32 and back side 34 isolate interior 36 from environmental conditions external to pouch 30 such as contaminants carried by air flow, moisture, etc. As a result of being shielded from external environmental conditions, interior 36 provides a closed, sterile environment. In use, user 10 connects catheter 12 to fill-drain tube 22 in the closed, sterile environment provided by interior 36 thereby satisfying the aseptic connection technique for the exchange of used and fresh dialysis fluid as described with reference to FIG. 2.

Figure 3:
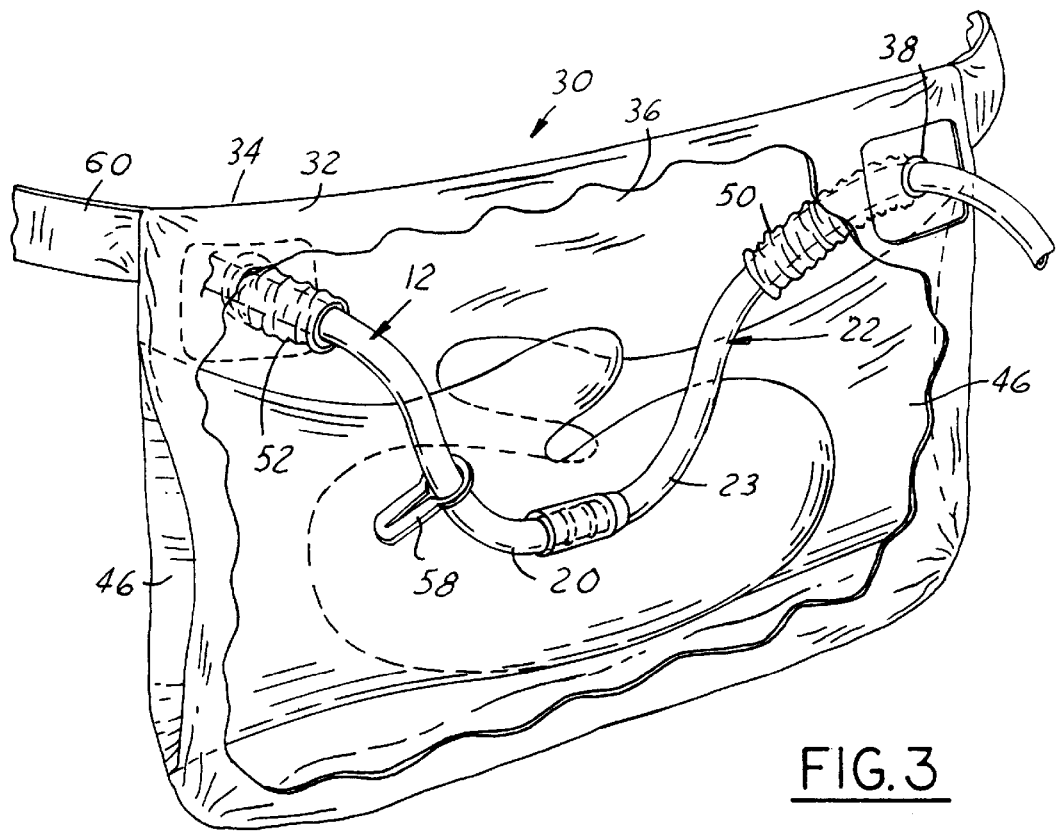
FIG. 3 illustrates a perspective cut-away view of the user wearable device which has a sealed interior for connecting the user's catheter to a fill-drain tube for feeding and draining dialysis fluid in accordance with the present invention.
Figure 4:
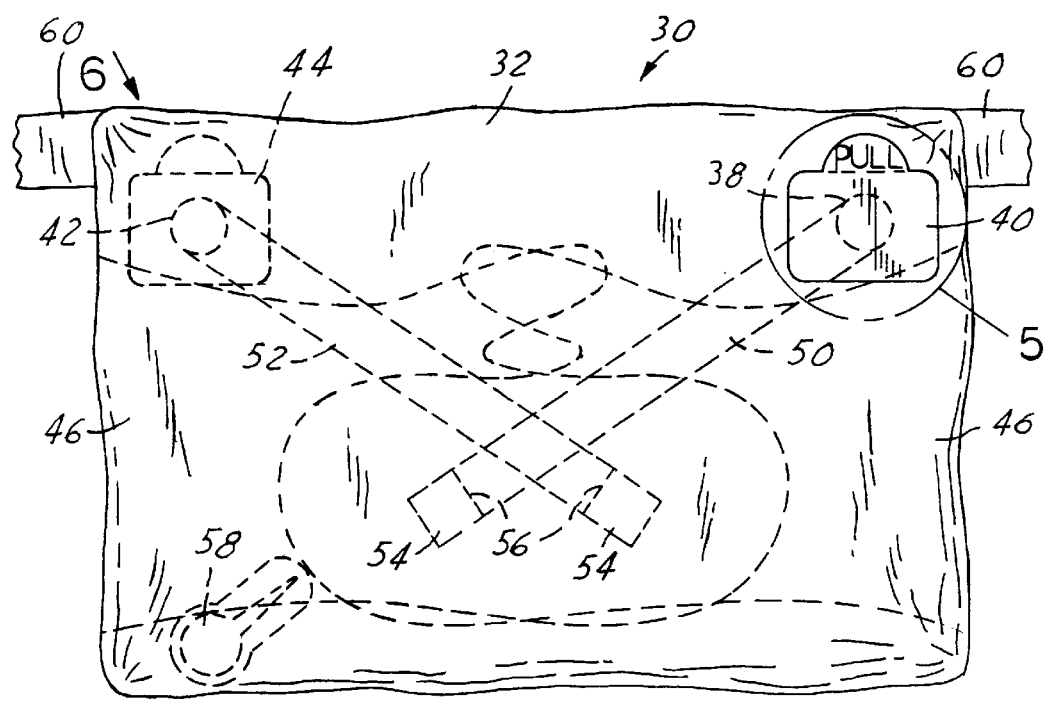
FIG. 4 illustrates the front side of the user wearable device facing away from the user showing in phantom the elements in the interior of the device.
Figure 7:
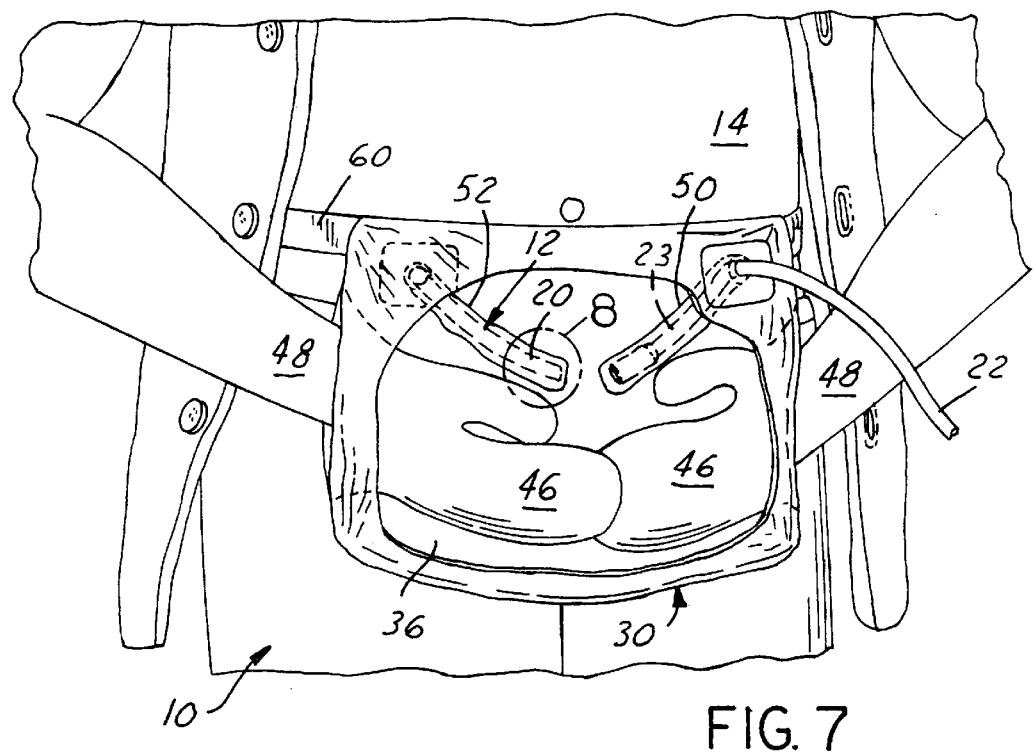
FIG. 7 illustrates the user's hands inserted into mittens which are in communication with the exterior of the user wearable device and are internally disposed within the interior of the user wearable device for connecting the user's catheter to the fill-drain tube within the interior of the user wearable device while the user is wearing the user wearable device.

Pouch 30 is intended to be worn around user's abdomen 14 as shown in FIG. 7 with front side 32 facing away from the user's abdomen and back side 34 facing towards the user's abdomen for performing an exchange of dialysis fluid. Front side 32 of pouch 30 includes a first exposeable opening 38. A first peel away covering element 40 such as a peel away seal covers first exposeable opening 38. User 10 peels first covering element 40 to expose first opening 38. User 10 then inserts first end 23 of fill-drain tube 22 through first opening 38 into interior 36 of pouch 30. Back side 34 of pouch 30 includes a second exposeable opening 42. A second peel away covering element 44 such as a peel away seal covers second exposeable opening 42. User 10 peels second covering element 44 to expose second opening 42. User 10 then inserts external end 20 of catheter 12 through second opening 42 into interior 36 of pouch 30. From the exterior of pouch 30, user 10 then clamps and manipulates catheter 12 and fill-drain tube 22 within interior 36 of the pouch to connect external end 20 of the catheter to first end 23 of the fill-drain tube. FIG. 3 best illustrates the connection between external end 20 of catheter 12 and first end 23 of fill-drain tube 22 within interior 36 of pouch 30.

In order to enable user 10 to manipulate catheter 12 and fill-drain tube 22 from the exterior of pouch 30, the pouch further includes a pair of hand covering elements 46. Hand covering elements 46 such as mittens, gloves, or the like are formed between front side 32 and back side 34 of pouch 30. Hand covering elements 46 are in communication with the exterior of pouch 30 and are internally disposed into interior 36 of the pouch for receiving the hands 48 of user 10 (shown best in FIG. 7). User 10 inserts his hands 48 into hand covering elements 46 in order to manipulate catheter 12 and fill-drain tube 22 contained within interior 36 of pouch 30 from the outside of the pouch in order to connect them together.

Pouch 30 also includes a fill-drain tube sleeve 50 connected to first exposeable opening 38 of front side 32. Fill-drain tube sleeve 50 extends from first exposeable opening 38 into interior 36 of pouch 30. Fill-drain tube sleeve 50 receives fill-drain tube 22 when the fill-drain tube is inserted through first exposeable opening 38. Similarly, pouch 30 further includes a catheter sleeve 52 connected to second exposeable opening 42 of back side 34. Catheter sleeve 52 extends from second exposeable opening 42 into interior 36 of pouch 30. Catheter sleeve 52 receives catheter 12 when the catheter is inserted through second exposeable opening 42.

Fill-drain tube sleeve 50 and catheter sleeve 52 extend from respective openings 38 and 42 towards one another within the middle portion of interior 36 of pouch 30. Fill-drain tube sleeve 50 and catheter sleeve 52 direct inserted fill-drain tube 22 and catheter 12 towards one another within the middle portion of interior 36 of pouch 30. Fill-drain tube sleeve 50 and catheter sleeve 52 are each sealed at their ends away from openings 38 and 42 by respective tear away elements 54. Tear away elements 54 are each connected by a perforation line 56 to the ends of fill-drain tube sleeve 50 and catheter sleeve 52.

Figure 8:
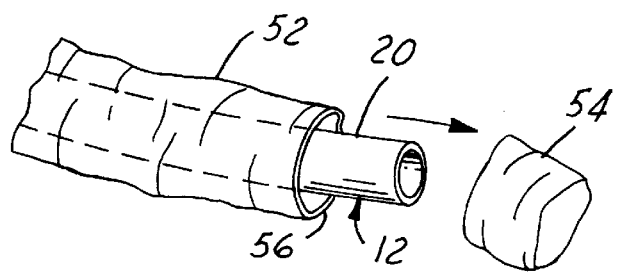
FIG. 8 illustrates the end of the catheter sleeve of the user wearable device being torn to expose the external end of the user's catheter.

User 10 tears away each tear away element 54 along its perforation line 56 to expose the ends of tubes (fill-drain and catheter) from their respective sleeves 50 and 52 within the middle portion of interior 36 of pouch 30. For instance, as shown in FIG. 8, tear away element 54 is torn along its perforation line 56 from catheter sleeve 52 to expose external end 20 of catheter 12. Similarly, tear away element 54 is torn along its perforation line 56 from fill-drain tube sleeve 50 to expose first end 23 of fill-drain tube 22. User 10 then uses hand covering elements 46 to manipulate from outside of pouch 30 the exposed first end 23 of fill-drain tube 22 and the exposed external end 20 of catheter 12 contained within interior 36 of pouch 30 to connect them together within the interior of the pouch. Instead of being provided with perforation lines 56, each element 54 may be configured to fold up and over the exterior surface of the ends of sleeves 50 and 52 and then be sealed down with a seal onto the exterior surfaces of the sleeve ends.

Figure 9:
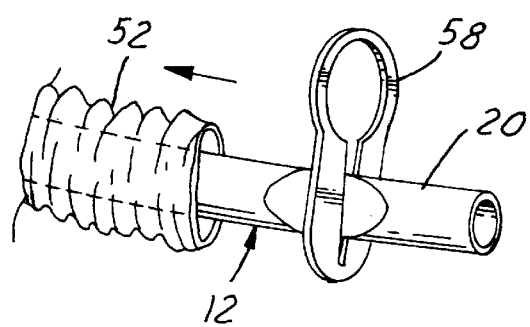
FIG. 9 illustrates the external end of the user's catheter being clamped by a clamping device disposed in the interior of the user wearable device.
Figure 10:
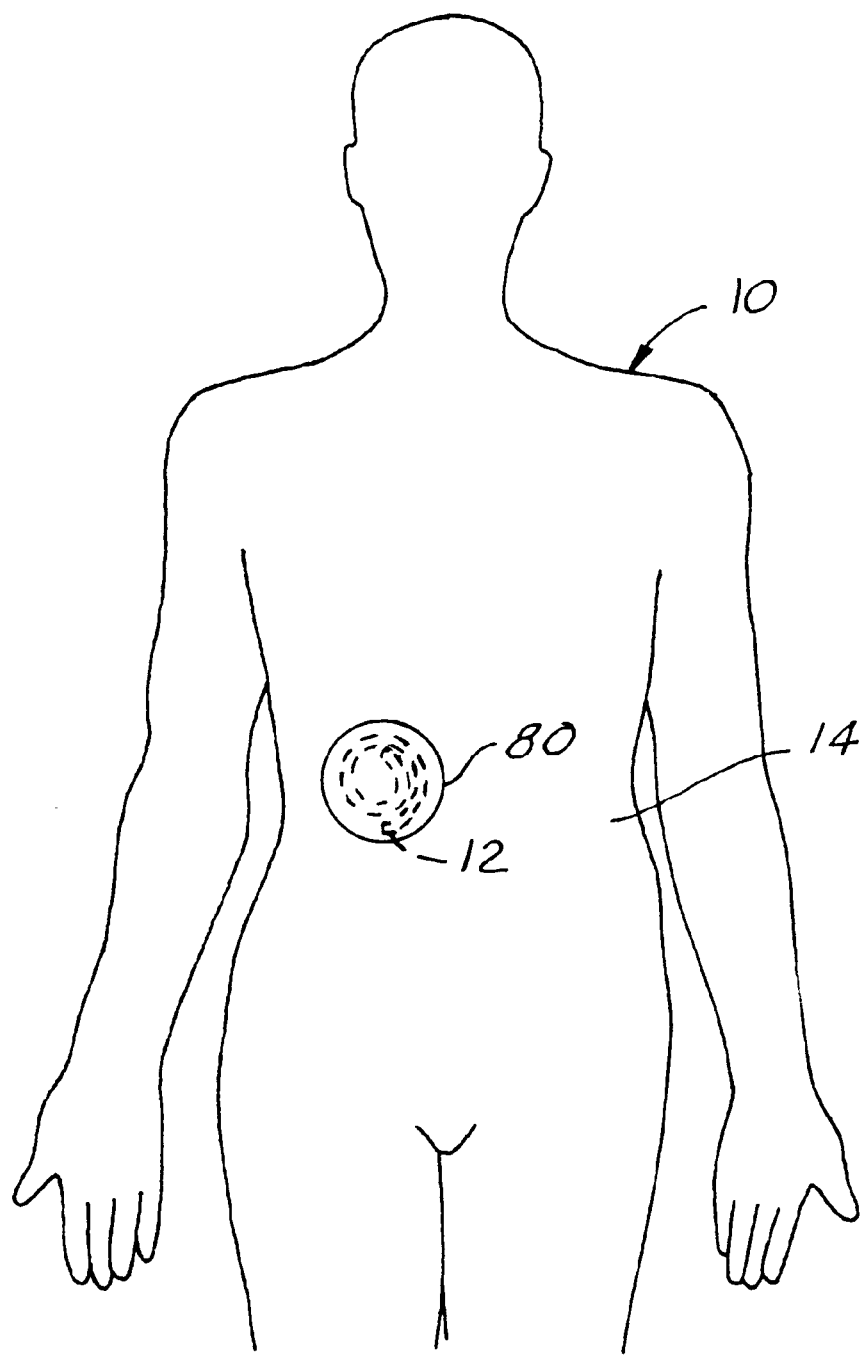
FIG. 10 illustrates a safety cap attachable to the user's abdomen for covering the user's catheter after completion of an exchange of used and fresh dialysis fluid.

Pouch 30 further includes a clamping device 58 for clamping external end 20 of catheter 12 during an exchange of used and fresh dialysis fluid. Clamping device 58 is contained within interior 36 of pouch 30 and is connected to one of the interior sides of front side 32 and back side 34. As best shown in FIG. 9, user 10 uses clamping device 58 to clamp catheter 12 as is typically done for performing CAPD. As is the case for the connection between catheter 12 and fill-drain tube 22, user 10 uses hand covering elements 46 to manipulate clamping device 58 from the outside of pouch 30.

In operation for performing a standard peritoneal dialysis exchange, user 10 clamps catheter 12 with clamping device 58 before the catheter is connected to fill-drain tube 22 to close the catheter. User 10 then opens fill bag 26 to allow some fresh dialysis fluid to fill from the fill bag into drain bag 28. User 10 then clamps off fill bag 26 with a fill bag clamping device to stop fresh dialysis fluid from feeding from the fill bag. User 10 then removes clamping device 48 to open the catheter in order to allow used dialysis fluid from peritoneal cavity 18 to drain into drain bag 28. Once the used dialysis fluid is drained, user 10 clamps off drain bag with a drain bag clamping device to prevent fluid from flowing into the drain bag and then removes the fill bag clamping device from fill bag 26 to allow fresh dialysis fluid to flow from the fill bag into the user's peritoneal cavity 18 via catheter 12.

Prior to use, interior 36 of pouch 30 provides a closed, sterile environment as first and second openings 38 and 42 are covered or sealed by respective covering elements 40 and 44 and the ends of sleeves 50 and 52 are sealed by respective tear away elements 54. During use, the closed, sterile environment provided by interior 36 of pouch 30 is left intact as only openings 38 and 42 are exposed to allow insertion of fill-drain tube 22 and catheter 12 into respective sleeves 50 and 52. Once inserted through openings 38 and 42, fill-drain tube 22 and catheter 12 effectively act as covering elements 40 and 44 and shield interior 36 of pouch 30 from external environmental conditions. After fill-drain tube 22 and catheter 12 are inserted into their respective sleeves 50 and 52 into interior 36 of pouch 30, then tear away elements 54 are torn away from the sleeves to expose the ends of fill-drain tube and catheter within the interior of the pouch. Thus, during the entire usage of pouch 30, interior 36 of pouch 30 provides a closed, sterile environment for effecting a connection between catheter 12 and fill-drain tube 20.

As shown best in FIG. 7, pouch 30 is intended to be worn by user 10. To this end, pouch 30 includes a pair of apron strings 60 or the like. Apron strings 60 are connected on opposing ends of pouch 30 to at least one of front side 32 and back side 34 and preferably connected to back side 34. Apron strings 60 are tied around user's abdomen 14 in order for the user to wear pouch 30. Back side 34 of pouch 30 may also include a breathable, mesh type fabric or plastic to provide a comfortable fit of the pouch with user's abdomen 14.

Pouch 30 is configured such that second opening 42 is aligned with the exit point of catheter 12 from user's abdomen 14 when the pouch is worn by user 10. This provides a comfortable and snug fit with user 10 and also uses the user's body to effectively seal second opening 42 when exposed. To this end, a medical type adhesive pad 62 is positioned around second opening 42 on back side 34 of pouch 30. Second covering element 44 covers adhesive pad 62 until the second covering element is peeled away.

In order to assist use of pouch 30, the elements of the pouch may be colored differently. For instance, front and back sides 32 and 34 may have a transparent color whereas elements contained within interior of pouch 30 such as sleeves 50 and 52 may be colored (same or different colors) to assist user 10 in recognizing the sleeves.

Further, in helping prevent infection of the exit point of catheter 12 on user's abdomen 14, a catheter safety cap 80 in accordance with the present invention may be provided. Safety cap 80 snaps on and off a ring attached to the user's abdomen 14. The ring includes a medical type adhesive for attaching around the exit point of catheter 12 on user's abdomen 14. User 10 snaps safety cap 80 on the ring to cover catheter 12 and the exit point of the catheter upon completion of an exchange of used and fresh dialysis fluid. In use, safety cap 80 prevents germs from traveling along catheter 12 through the exit point into user's peritoneal cavity.

In essence, the user wearable device or pouch 30 functions as a sterile, pathogenic-free environment for containing catheter 12 protruding from the user's abdomen 14, fill-drain tube 22, and any clamping devices 58 necessary during the hook-up phase of a peritoneal dialysis fluid exchange. Pouch 30 allows user 10 to manipulate the elements 12, 22, 58, etc., contained within interior 36 of the pouch from outside of the pouch in order to complete the peritoneal dialysis connections in any environmental setting.

Thus it is apparent that there has been provided, in accordance with the present invention, a user wearable device such as a pouch which provides a sterile environment for connecting a catheter to a fill-drain tube for feeding and draining dialysis fluid that fully satisfies the objects, aims, and advantages set forth above. While the present invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

What is claimed is:

1. A device intended to be worn by a user for connecting a catheter of the user to a fill-drain tube for performing an exchange of dialysis fluid, the device comprising:

a pouch having an interior formed by connected front and back sides, the front side of the pouch having an exposeable opening for inserting a fill-drain tube into the interior of the pouch, the back side of the pouch having an exposeable opening far inserting a catheter into the interior of the pouch; and a catheter clamp connected to one of the front and back sides of the pouch within the interior of the pouch.

2. The device of claim 1 further comprising:

at least one internally disposed hand covering element in communication with the exterior of the pouch for receiving at least one of the user's hands in order to enable the user to connect the catheter to the fill-drain tube within the interior of the pouch for performing an exchange of dialysis fluid.

3. The device of claim 2 wherein:

the at least one internally disposed hand covering element includes a pair of mittens.

4. A device intended to be worn by a user for connecting a catheter of the user to a fill-drain tube for performing an exchange of dialysis fluid, the device comprising:

a pouch having an interior formed by connected front and back sides, the front side of the pouch having an exposeable opening for inserting a fill-drain tube into the interior of the pouch, the back side of the pouch having an exposeable opening for inserting a catheter into the interior of the pouch; and a fill-drain tube sleeve connected to the exposeable opening of the from side of the pouch and extending into the interior of the pouch for receiving the fill-drain tube when the fin-drain tube is inserted into the interior of the pouch.

5. The device of claim 1 further comprising:

a catheter sleeve connected to the exposeable opening of the back side of the pouch and extending into the interior of the pouch for receiving the catheter when the catheter is inserted into the interior of the pouch.

6. The device of claim 1 wherein:

the exposeable openings of the front and back sides of the pouch include peel away seals.

7. The device of claim 1 further comprising:

attachment means connected to the pouch for attaching the pouch to the user.

8. The device of claim 7 wherein:

the attachment means include a pair of strings connected to at least one of the front and back sides of the pouch for attaching the pouch to the user.

9. The device of claim 7 wherein:

the attachment means include an adhesive attached to the back side of the pouch.

10. The device of claim 9 wherein:

the adhesive is positioned around the exposeable opening of the back side of the pouch.

11. The device of claim 1 wherein:

the exposeable openings each include a peel away covering element.

12. The device of claim 1 wherein:

the pouch includes plastic.

13. A peritoneal dialysis system for a user having a catheter the system comprising:

a fill bag for feeding dialysis fluid;

a drain bag for draining dialysis fluid;

a fill-drain tube connected at a first end by a Y connection to the fill bag and the drain bag; and a user wearable device having a closed pouch, the pouch having a first exposeable opening for inserting a second end of the fill-drain tube into the pouch and a second exposeable opening for inserting a catheter of a user wearing the pouch into the pouch in order to enable the catheter and the second end of the fill-drain tube to be connected together within the pouch by manipulation from outside of the pouch, the pouch further having a catheter clamp connected to the pouch within the interior of the pouch.

14. A device intended to be worn by a user for connecting a catheter connected to a user to a fill-drain tube for performing an exchange of dialysis fluid, the device comprising:

a pouch having a closed interior, a first exposeable opening for inserting a fill-drain tube from an exterior of the pouch into the interior of the pouch, and a second exposeable opening for inserting a catheter of a user from the exterior of the pouch into the interior of the pouch;

an internally disposed hand covering element in communication with the exterior of the pouch for receiving a hand of the user in order to enable the user to connect the catheter to the fill-drain tube within the interior of the pouch for performing an exchange of dialysis fluid;

a fill-drain tube sleeve connected to the first exposeable opening and extending into the interior of the pouch for receiving the fill-drain tube when the fill-drain tube is inserted into the interior of the pouch; and a catheter sleeve connected to the second exposeable opening and extending into the interior of the pouch for receiving the catheter when the catheter is inserted into the interior of the pouch.

15. The device of claim 14 further comprising:

an adhesive positioned around the periphery of the second exposeable opening for attaching the pouch to the user by attaching the second exposeable opening to the user's abdomen around the catheter connected to the user.

16. The device of claim 14 wherein:

at least one of the pouch, the hand covering element, the fill-drain tube, and the catheter sleeve is colored differently.

17. The device of claim 14 further comprising:

a catheter clamp positioned within the interior of the pouch for clamping the catheter.

18. The device of claim 14 wherein:

the pouch and the hand covering element are colored differently.

19. The device of claim 14 wherein:

the first and second exposeable openings each include respective peel away covering elements.

20. A device intended to be worn by a user for connecting an external end of a catheter connected to a user to a first end of a fill-drain tube connected at a second end to a fill bag and a drain bag for performing an exchange of dialysis fluid, the device comprising:

a pouch having a closed interior, a first exposeable opening for inserting a first end of a fill-drain tube from an exterior of the pouch into the interior of the pouch, and a second exposeable opening for inserting an external end of a catheter of a user from the exterior of the pouch into the interior of the pouch;

a pair of band covering elements in communication with the exterior of the pouch and internally disposed into the interior of the pouch for receiving the hands of the user in order to enable the user to connect the external end of the catheter to the first end of the fill-drain tube within the interior of the pouch for performing an exchange of dialysis fluid;

a fill-drain tube sleeve connected to the first exposeable opening and extending into the interior of the pouch far receiving the first end of the fill-drain tube when the first end of the fill-drain tube is inserted into the interior of the pouch; and a catheter sleeve connected to the second exposeable opening and extending into the interior of the pouch for receiving the external end of the catheter when the external end of the catheter is inserted into the interior of the pouch.

21. A method for performing an exchange of used and fresh dialysis fluid on a user having a catheter, the method comprising:

providing a closed pouch having a first exposeable opening and a second exposeable opening, the closed pouch having a catheter clamp connected to the pouch within the interior of the pouch;

inserting a catheter of the user into pouch through the first exposeable opening;

inserting a fill-drain tube into the pouch through the second exposeable opening;

connecting the catheter to the fill-drain tube in the pouch by manipulation of the catheter and the fill-drain tube from outside of the pouch; and clamping the catheter with the catheter clamp prior to connecting the catheter to the fill-drain tube.

22. The method of claim 21 further comprising:

attaching the pouch to the user after the catheter is inserted into the pouch through the first exposeable opening.

23. The method of claim 22 wherein:

attaching the to the user includes using an adhesive positioned around the first exposeable opening on the outside of the pouch and attaching the adhesive to the user around the catheter.

24. The method of claim 21 wherein:

connecting fill-drain tube includes using a pair of hand covering elements in communication with the exterior of the pouch and internally disposed into the interior of the pouch for receiving the hands of the user.

25. The method of claim 21 further comprising:

exposing the first exposeable opening prior to inserting the catheter into the pouch through the first exposeable opening.

26. The method of claim 21 further comprising:

exposing the second exposeable opening prior to inserting the fill-drain tube into the pouch through the second exposeable opening.

27. The method of claim 21 further comprising:

removing the catheter clamp from the catheter after connecting the catheter to the till-drain tube.

* * * * *

UNITED STATES PATENT AND TRADEMARK OFFICE
CERTIFICATE OF CORRECTION

PATENT NO. : 6,682,507 B2
DATED : January 27, 2004
INVENTOR(S) : Douglas H. Irish It is certified that error appears in the above-identified patent and that said Letters Patent is hereby corrected as shown below:

Column 9,
Line 23, delete "far" and insert -- for --.

Column 11,
Line 20, delete "band" and insert -- hand --.
Line 26, delete "far" and insert -- for --.

Column 12,
Line 18, after "the" insert -- pouch --.

Signed and Sealed this

Fourth Day of May, 2004

JON W. DUDAS
*Acting Director of the United States Patent and Trademark Office*